US00PP26572P3

(12) United States Plant Patent
Acosta

(10) Patent No.: US PP26,572 P3
(45) Date of Patent: Apr. 5, 2016

(54) AVOCADO TREE NAMED 'VICTOR'

(50) Latin Name: ***Persea americana mille* var.**
Varietal Denomination: Victor

(71) Applicant: Acosta Farms, Inc., Miami, FL (US)

(72) Inventor: Alcides Acosta, Coral Gables, FL (US)

( * ) Notice: Subject to any disclaimer, the term of this patent is extended or adjusted under 35 U.S.C. 154(b) by 3 days.

(21) Appl. No.: 13/998,168

(22) Filed: Oct. 8, 2013

(65) Prior Publication Data

US 2015/0101089 P1 Apr. 9, 2015

(51) Int. Cl.
*A01H 5/08* (2006.01)

(52) U.S. Cl.
USPC ..... Plt./200
CPC ..... *A01H 5/0818* (2013.01)

(58) Field of Classification Search
USPC ..... Plt./200
See application file for complete search history.

*Primary Examiner* — Keith Robinson
(74) *Attorney, Agent, or Firm* — Michael C. Cesarano, P.A.

(57) ABSTRACT

The 'Victor' avocado is of medium size, average 16-22 ounces and being about 4.5-5 inches in diameter and 6 inches in length. The fruit matures and can be picked in late February to late March. The fruit is an ovate berry having a seed that is tight in the cavity and is 2.5 to 3.25 inches long and dark brown in color.

3 Drawing Sheets

Scientific name: *Persea americana mille* var. 'Victor'.

BRIEF SUMMARY OF THE INVENTION

The tree is in a cultivated 40 acre avocado grove located in Miami-Dade County, Fla. The tree is estimated to be 30 years old and has been in production for at least 20 years. Its origin is unknown. Its fruit can be stored at temperatures above 50° Fahrenheit.

Parentage is unknown as the tree was discovered, and is of a wild nature. The tree has been observed for approximately 4 years. An analysis of the microsatellite pattern from this avocado against 13 known varieties ('Lula' (not patented), 'Simmonds' (not patented), 'Monroe' (U.S. Plant Pat. No. 261), 'Choquette' (not patented), 'Semil-34' (not patented), 'Semil-43' (not patented), 'Melendez' (not patented), 'Hall' (not patented), 'Booth' (not patented), 'Hardee' (not patented), 'April' (not patented), 'Carla' (U.S. Plant Pat. No. 16,594), and 'Pollock' (not patented)) revealed no matches.

Asexual propagation was attained in 2009 in Miami-Dade County, Fla. when the plant was approximately 26 years old. Asexual reproduction was achieved by grafting cuttings of the tree onto new avocado seedlings. The fruit is ripened and is sufficient for harvesting in late February to late March. 'Victor' presents resistance to *Carpospores purpurea* pathogens.

BRIEF DESCRIPTION OF THE DRAWINGS

FIG. 1 shows the trunk at a lower portion of the 'Victor' avocado tree.

FIG. 2 shows the midlevel portion of the 'Victor' avocado tree.

DETAILED BOTANICAL DESCRIPTION

Figure 3:
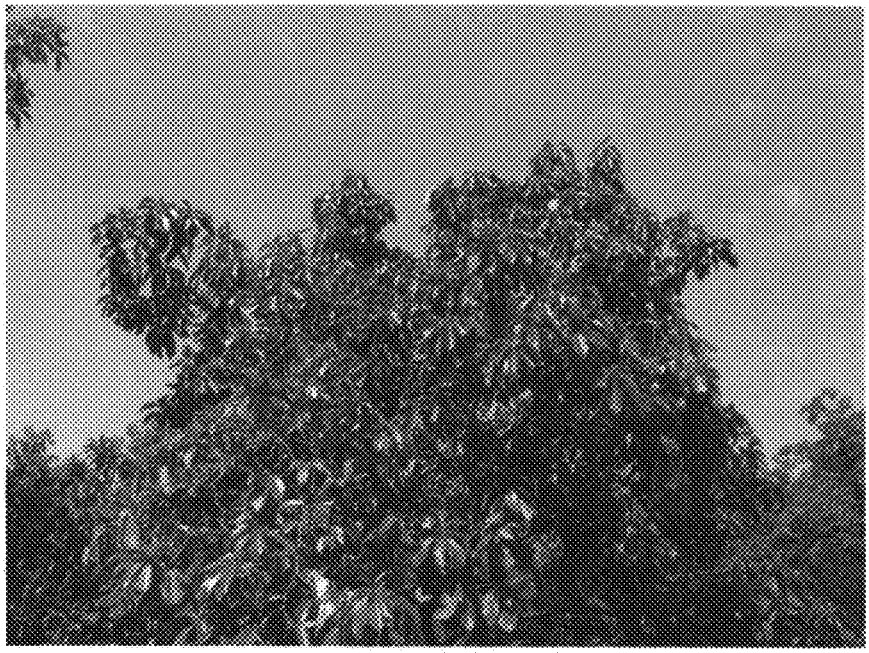
FIG. 3 shows the upper portion of the 'Victor' avocado tree.
Figure 4:
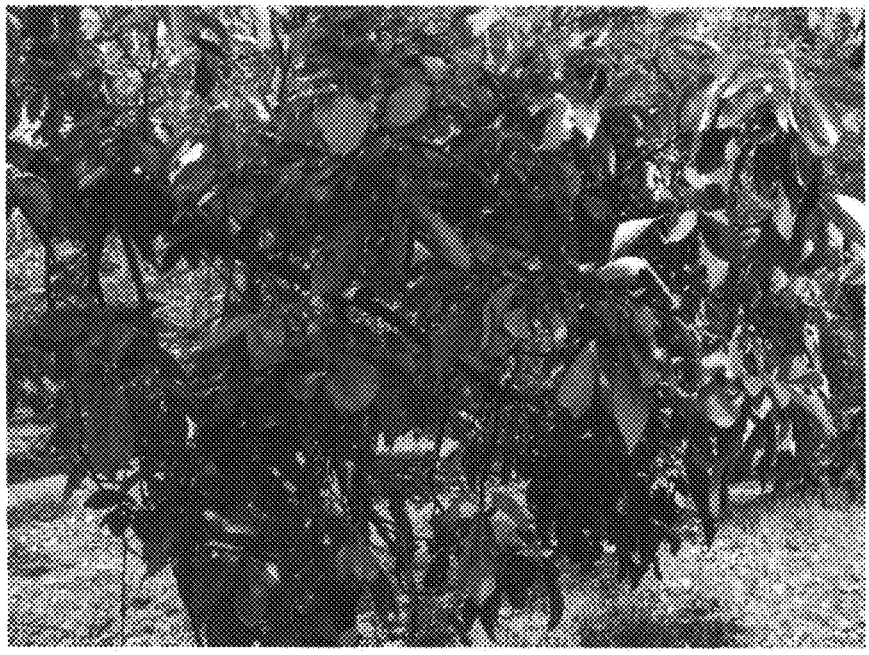
FIG. 4 shows a detailed view of the leaf of the 'Victor' avocado tree.

Botanical descriptions follow the terminology used in *Exotica Pictorial Cyclopedia of Exotic Plants*, A. B. Graf, p. 1834, "Botanical Terms Illustrated." Colors are described using the HEX value designation obtained from the web site www.cloford.com.

The tree presents a vigorous upright growth with a spread of 18' and 25' high (before pruning). As shown in FIG. 1, the diameter of the main trunk is 26", tapering as it extends straight and upward to the pinnacle of the tree. At three feet above the ground, the trunk has a circumference of 36" and a diameter of 11.5". As shown in FIG. 1, the main trunk splits into 4 branches, two of which are scaffold limbs of approximately 7" in diameter, with smaller branches each being about 3-4 inches in diameter with the vertical sub trunk splitting into smaller branches. The limbs range from 3-10' from the main axis of the tree. The bark of the trunk is corky and rough being light brown in color with new shoots being green in color and the foliage being dark green at maturity and burgundy at a young stage. Lenticels are prominent on limbs of green wood but are obscured as bark ages and becomes corkier. Color is an indeterminate brown to greenish brown owing to a repeated copper hydroxide spray regimen.

The leaves are obovate and have a smooth upper surface marked by a lighter venation that is very slightly raised. The leaf tip is acuminate to slightly cuspidate. The leaf base is predominately acuminate. The margin is entire and undulate. The upper leaf color is "olivedrab 3" (yellow green), HEX value #9ACD32. The underside of the leaves are a shade lighter in color, "dark olive green," HEX value #CAFF70, and veins are predominantly raised. The number of veins from mid-rib average 10.

The leaves are dark green and vary in width from 2" to 4" (5 cm to 10 cm), having an average width of 3.3" (8.5 cm), and vary in length from 5.75" to 9" (14.6 cm to 22.9 cm), having an average length of 6.8" (7.2 cm). They have a smooth upper surface that becomes leathery in texture as they mature, as appears in FIGS. 1, 2, 3, and 4. The foliage is sparse near the ground, becoming more dense toward the upper regions of the tree. Petiole lengths range from 2-3" (5 to 7.6 cm), with the average length being 2.6" (6.6 cm). Typical observed petiole diameter is 3.4-3.6 mm. Internode length is 0.5-0.75" (1.27-1.9 cm). Leaves alternate and have an angle with the stem of 45°-75° depending on the level of sunlight exposure. There is no anise odor to the leaves.

Buds are yellow-green in color, have an average length of 7-10 mm, average width of 4 mm, and a Lancelot to Lancelot-oblong shape with a rounded base and acute tip. Pedicels are green-yellow in color and average 6 mm in length and 1.3 mm in width with an average diameter of 1-2 mm. Peduncles range from 42 mm to 153 mm and average about 87 mm and are yellow green in color. Typical observed flower depth is 7.7-8 mm.

The flowers of this plant have 3 lobes that are approximately 6.5-6.7 mm in length and 2 mm in width. The texture is smooth and densely silk tomentose is found on both surfaces. The shape is apex acute with a flattened base.

Figure 5:
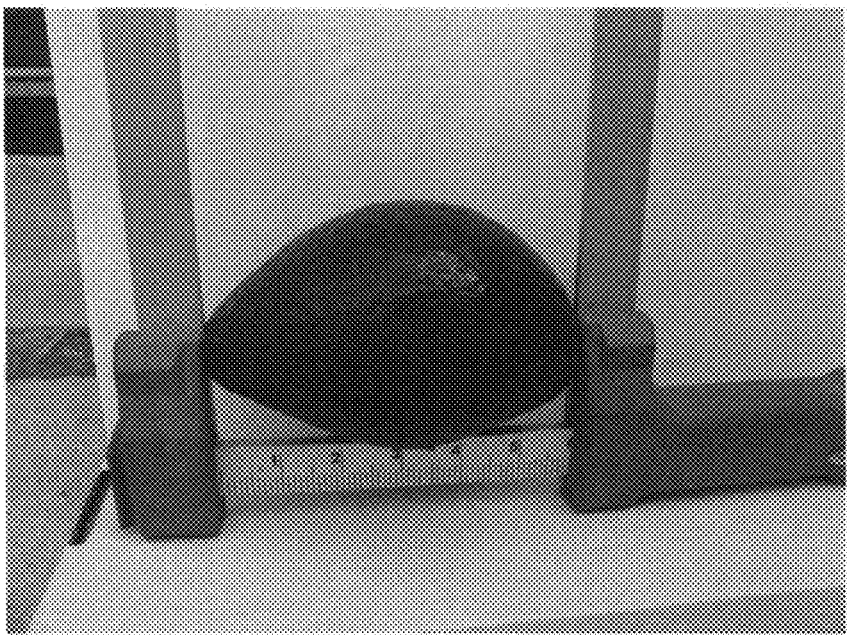
FIG. 5 shows the scale in inches of a typical fruit of the 'Victor' avocado tree measured against a ruler.
Figure 6:
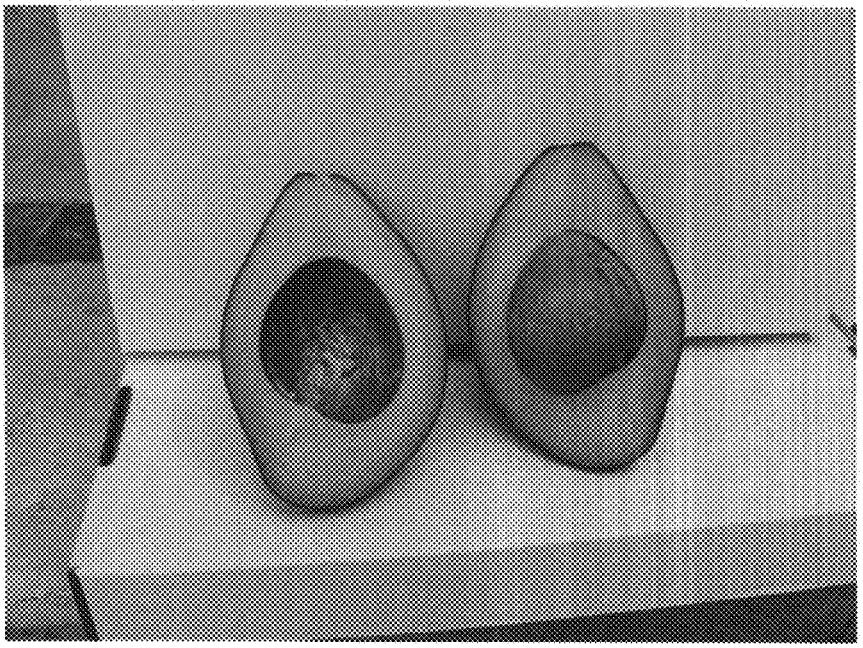
FIG. 6 shows the color and internal configuration of the fruit and the seed of the 'Victor' avocado tree.

The tree is distinguished from other commercial avocado varieties by virtue of the late season of harvest. As shown in FIG. 5, the fruit shape is an ovate berry that matures in late February to late March, and that ranges from 4"-5" in diameter and 6" in length, and whose skin exhibits a high gloss. The ovate shape of the fruit is easily distinguishable from the fruit of the 'Nico' avocado tree claimed in co-pending application Ser. No. 13/998,090, whose shape is distinctly more spherical, and whose skin exhibits a medium gloss. As shown in FIG. 6, the interior of the fruit is seen to have a mesocarp color that is green near the shell and yellow near the seed cavity. The seed is round, weighing about 6.9-7.2 oz, depending on overall fruit size, having a diameter between 2.5 and 3.25". The seed is tight in the cavity and is dark brown in color.

The plant produces fruit at a medium-high volume, averaging about 250-300 lbs per year. The tree's winter hardness is 9B. Avocado shelf life is several weeks, and the fruit can be stored above 50°. The fruit naturally ripens once placed at room temperature or about 5-8 days after harvesting.

The flowers are not fragrant. The tree blooms in March and the blooms are of the A type. Fruit matures and can be picked in late February or March of the following year. The fruit weights are between 16 and 22 ounces with the diameter averaging 4.5-5 inches.

The fruit is full in flavor and buttery in texture. The skin is glossy, moderately rough, and peels easily.

The invention claimed is:

1. A new and distinct variety of avocado tree substantially as described and illustrated and characterized as to novelty by its overall good eating qualities, its medium size and its being ready to be picked in late February to late March.

* * * * *

Fig. 1
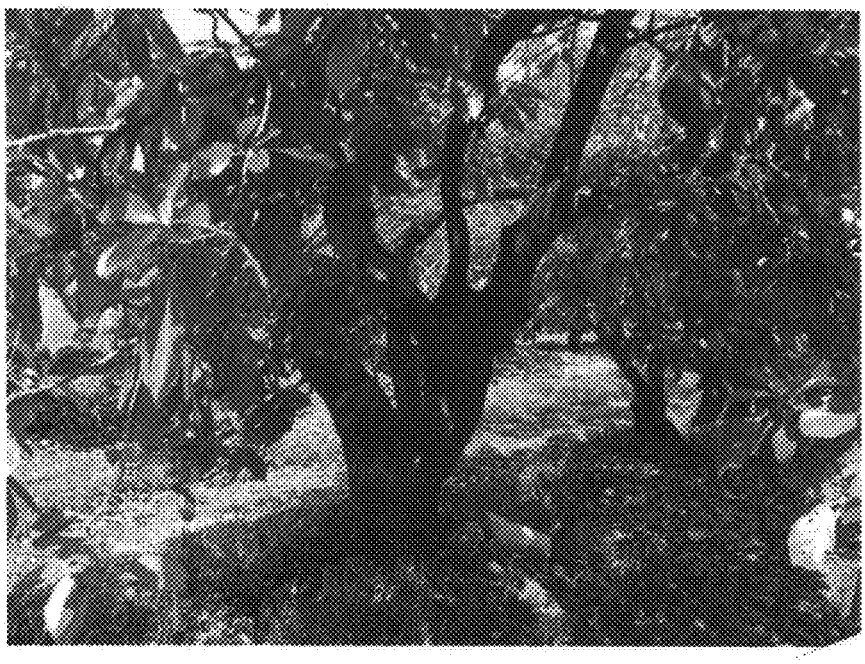
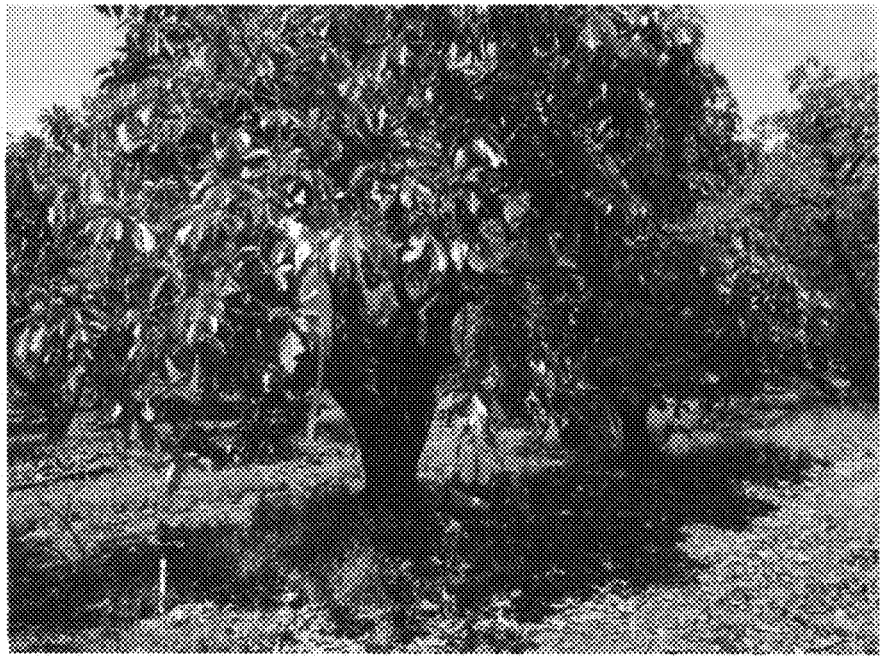
Fig. 2